(12) United States Patent
Imagawa et al.

(10) Patent No.: US 10,499,885 B2
(45) Date of Patent: Dec. 10, 2019

(54) ULTRASOUND SYSTEM AND METHOD, AND ULTRASOUND PROBE

(71) Applicant: Hitachi, Ltd., Chiyoda-ku, Tokyo (JP)

(72) Inventors: Kengo Imagawa, Tokyo (JP); Yutaka Igarashi, Tokyo (JP); Toru Yazaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1029 days.

(21) Appl. No.: 14/898,675

(22) PCT Filed: May 30, 2014

(86) PCT No.: PCT/JP2014/064368
§ 371 (c)(1),
(2) Date: Dec. 15, 2015

(87) PCT Pub. No.: WO2014/208269
PCT Pub. Date: Dec. 31, 2014

(65) Prior Publication Data
US 2016/0120516 A1    May 5, 2016

(30) Foreign Application Priority Data

Jun. 25, 2013    (JP) .................................. 2013-132455

(51) Int. Cl.
*A61B 8/00*    (2006.01)
*A61B 8/08*    (2006.01)
(Continued)

(52) U.S. Cl.
CPC ................. *A61B 8/56* (2013.01); *A61B 8/08* (2013.01); *A61B 8/145* (2013.01); *A61B 8/4488* (2013.01);
(Continued)

(58) Field of Classification Search
CPC ......... A61B 8/08; A61B 8/145; A61B 8/4488; A61B 8/4494; A61B 8/465; A61B 8/5207;
(Continued)

(56) References Cited

U.S. PATENT DOCUMENTS

2002/0007118 A1    1/2002  Adachi et al.
2004/0015079 A1*   1/2004  Berger .................. A61B 8/546
                                                         600/437
(Continued)

FOREIGN PATENT DOCUMENTS

JP    2002-165796 A    6/2002
JP    2002-248100 A    9/2002
(Continued)

OTHER PUBLICATIONS

International Search Report (PCT/ISA/210) issued in PCT Application No. PCT/JP2014/064368 dated Jul. 8, 2014 with English translation (three pages).

*Primary Examiner* — Amelie R Gillman
(74) *Attorney, Agent, or Firm* — Crowell & Moring LLP

(57) ABSTRACT

An objective of the present invention is to provide an ultrasound system which can correct a positive-negative asymmetry in pulse inversion (PI) and obtain a high-image quality ultrasound image. To carryout an asymmetry correction of a transmission assembly circuit comprising an oscillation adjustment amplifier (10) and an ultrasound oscillator array (90), correction data obtained in a calibration mode is stored in a correction memory (46), and positive-negative asymmetry of an overall receiving assembly circuit comprising a computation unit (45) is corrected in a diagnostic mode of the device using the correction data.

11 Claims, 8 Drawing Sheets

(51) Int. Cl.
  *G01S 15/89* (2006.01)
  *G01S 7/52* (2006.01)
  *A61B 8/14* (2006.01)

(52) U.S. Cl.
  CPC .............. *A61B 8/5207* (2013.01); *A61B 8/58* (2013.01); *G01S 7/52033* (2013.01); *G01S 15/8927* (2013.01); *G01S 15/8963* (2013.01); *A61B 8/4494* (2013.01); *A61B 8/465* (2013.01); *G01S 7/52038* (2013.01); *G01S 15/8925* (2013.01)

(58) Field of Classification Search
  CPC ......... A61B 8/56; A61B 8/58; G01S 15/8925; G01S 15/8927; G01S 15/8963; G01S 7/52033; G01S 7/52038
  See application file for complete search history.

(56) References Cited

U.S. PATENT DOCUMENTS

| | | | |
|---|---|---|---|
| 2005/0148874 A1* | 7/2005 | Brock-Fisher | G01S 7/52049 600/447 |
| 2007/0106159 A1 | 5/2007 | Iwama | |
| 2013/0338485 A1* | 12/2013 | Mougenot | A61B 8/4494 600/411 |
| 2013/0338501 A1* | 12/2013 | Clingman | A61B 8/0825 600/440 |

FOREIGN PATENT DOCUMENTS

| | | |
|---|---|---|
| JP | 2002-369817 A | 12/2002 |
| JP | 2006-217944 A | 8/2006 |
| JP | 2007-117668 A | 5/2007 |
| JP | 2011-136224 A | 7/2011 |

\* cited by examiner

ULTRASOUND SYSTEM AND METHOD, AND ULTRASOUND PROBE

TECHNICAL FIELD

The present invention relates to an ultrasound system, and specifically, the technology aiming at high image quality of the ultrasound system utilizing a pulse inversion method.

BACKGROUND ART

The pulse inversion (PI) method has been known as the method for achieving high image quality of the ultrasound image. The PI method is called phase inversion method as the technique for ultrasound imaging with a harmonic content (harmonic) by utilizing nature of the ultrasound resulting from irradiating the living body organ with ultrasound at the single frequency. Specifically, upon ultrasound irradiation, the fundamental wave of the reflection ultrasound reflects at the same frequency with the same polarity as the irradiated ultrasound. On the contrary, the harmonic content of the reflection ultrasound reflects with monopolar regardless of polarity of the irradiated ultrasound. More specifically, a first reflection ultrasound (including the first fundamental wave content and the first harmonic content) as a result of irradiation of the first transmission waveform (positive electrode) is received, and a second reflection ultrasound (including the second fundamental wave content and the second harmonic content) as a result of irradiation of the second transmission waveform (negative electrode) is received, which has been derived from reversing polarity of the first transmission waveform (or phase shift at 180°). Addition of the first and the second reflection ultrasounds will offset the first and the second fundamental wave contents, making the first and the second harmonic contents doubled. Consequently, the PI method is carried out on the assumption that the sum of the first transmission waveform (positive electrode) and the second transmission waveform (negative electrode) is zero with respect to those frequency contents such as the fundamental wave and the harmonic content. If the assumption is ineffective, image quality is deteriorated, or in some cases, artifact (false image) is generated. In the transmission-reception circuit system of the actual configuration of the device, the positive-negative asymmetry (the sum of the first and the second transmission waveforms is not zero) is caused by various factors.

Various proposals for retaining the positive-negative symmetry have been made by, for example, Patent Literature 1 disclosing the transmission circuit suitable for carrying out the PI method, Patent Literature 2 disclosing structure of the oscillator for efficiently receiving the harmonic content, and Patent Literature 3 disclosing the method of processing the reception signal utilizing the filtering method.

CITATION LIST

Patent Literature

PTL 1: Japanese Unexamined Patent Application Publication No. 2007-117668
PTL 2: Japanese Unexamined Patent Application Publication No. 2002-248100
PTL 3: Japanese Unexamined Patent Application Publication No. 2002-369817

SUMMARY OF INVENTION

Technical Problem

Generally in the transmission circuit which drives the oscillator for ultrasound transmission, the respective waveforms of the positive/negative electrodes become asymmetrical because of characteristic differences in the P-type and N-type transistors that constitute the circuit. In consideration of variation in the parts and elements, it is difficult to compensate for the positive-negative asymmetry of a plurality of transmission circuits in the ultrasound system and the ultrasound probe. Since the ultrasound oscillator as the load of the transmission circuit transmits the ultrasound in accordance with transmission waveform of the positive/negative electrode from the transmission circuit, and the ultrasound oscillator exhibits nonlinear characteristic, asymmetry of the transmission waveform cannot be compensated. Furthermore, it is difficult for the unit for computing the reception signal to compensate for the asymmetry owing to characteristic of the transmission circuit, and nonlinearity of the oscillator.

It is an object of the present invention to provide an ultrasound system, and a method, and an ultrasound probe, which ensure acquisition of the ultrasound image with high quality utilizing the pulse inversion method by solving the aforementioned problems.

Solution to Problem

The aforementioned object is accomplished by the present invention which provides an ultrasound system including a transmission unit which transmits a first transmission signal and a second transmission signal obtained by polarity inversion of the first transmission signal, an ultrasound probe which transmits an ultrasound based on the first transmission signal and the second transmission signal from the transmission unit, and receives an ultrasound as a reflection ultrasound, a reception unit which receives a first reception signal and a second reception signal corresponding to the first transmission signal and the second transmission signal based on the reflection ultrasound received by the ultrasound probe, and a storage unit which stores correction data for correcting a positive-negative asymmetry based on an addition result of the first reception signal and the second reception signal in a calibration mode. The reception unit executes a correction computation using the addition result of the first reception signal and the second reception signal, and the correction data stored in the storage unit in a diagnostic mode.

The object is accomplished by the present invention which provides an ultrasound diagnostic method including the steps of transmitting a first transmission signal and a second transmission signal obtained by polarity inversion of the first transmission signal from an ultrasound probe, receiving a reflection ultrasound by the ultrasound probe, which has been transmitted based on the first transmission signal and the second transmission signal, and retaining an addition result derived from adding a first reception signal and a second reception signal corresponding to the first transmission signal and the second transmission signal based on the received reflection ultrasound in a calibration mode as correction data for correcting a positive-negative asymmetry, and carrying out a correction computation utilizing the addition result of the first reception signal and the second reception signal, and the retained correction data in a diagnostic mode.

The object is accomplished by the present invention which provides an ultrasound probe including a connector capable of connecting a transmission unit for transmitting a first transmission signal and a second transmission signal obtained by polarity inversion of the first transmission signal, and a reception unit for receiving a first reception signal and a second reception signal corresponding to the first transmission signal and the second transmission signal, an ultrasound probe array which transmits the ultrasound based on the first transmission signal and the second transmission signal from the transmission unit, and receives an ultrasound as a reflection ultrasound, and a storage unit which stores correction data for correcting a positive-negative asymmetry based on an addition result of the first reception signal and the second reception signal in reference to the reflection ultrasound in a calibration mode.

Advantageous Effects of Invention

The present invention ensures high quality ultrasound image utilizing the pulse inversion (PI) method.

DESCRIPTION OF EMBODIMENTS

Figure 9:
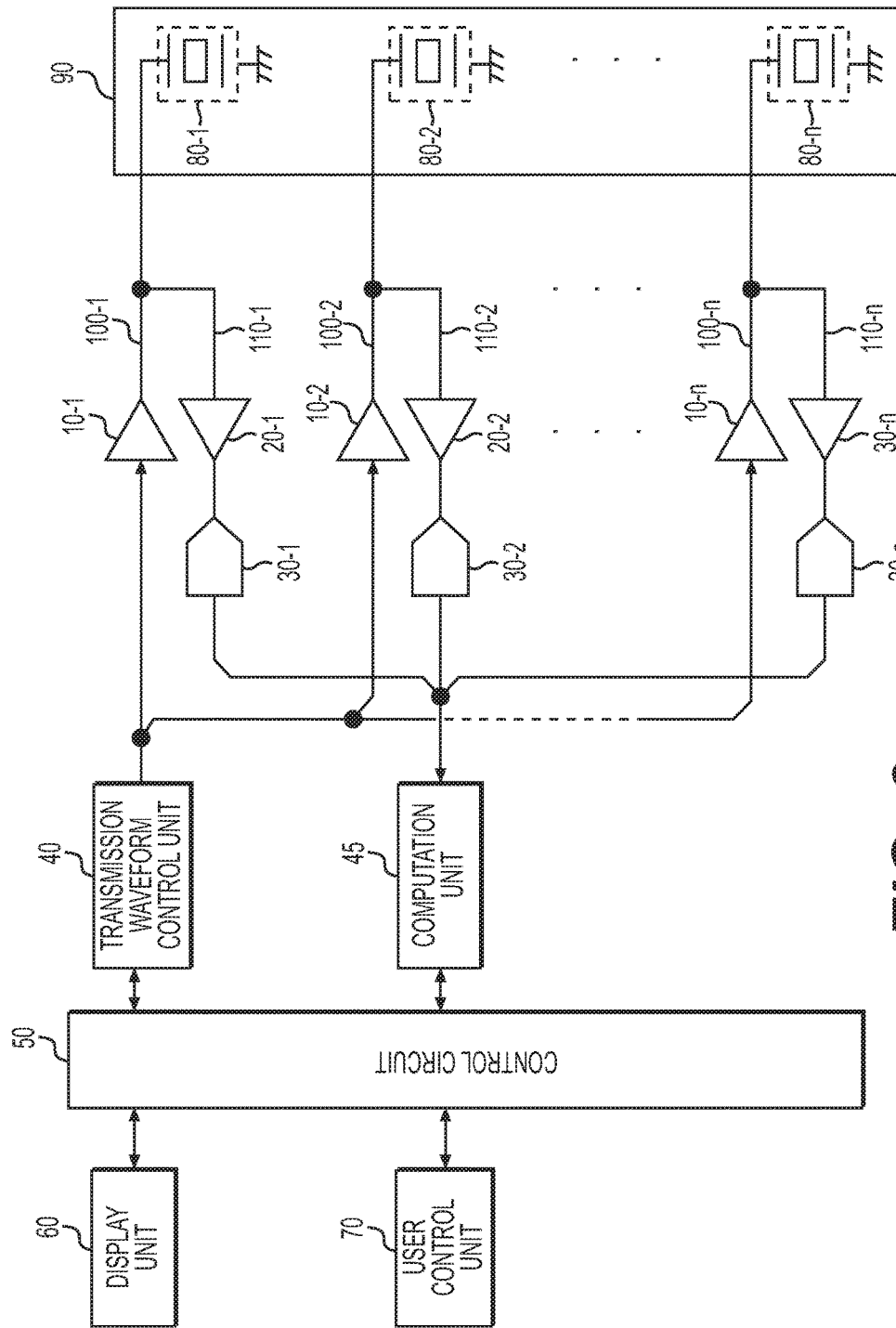
FIG. 9 is a view representing an exemplary structure of a transmission-reception circuit of a generally employed ultrasound system.

Before explanation of the respective embodiments according to the present invention, described is an exemplary structure of the transmission-reception circuit of a generally employed ultrasound system capable of carrying out the pulse inversion (PI) method referring to FIG. 9. Referring to the drawing, upon instruction of diagnosis to a control circuit 50 via a user control unit 70, the control circuit 50 constituted by the central processing unit (CPU) follows the instruction by outputting a transmission reference signal to a transmission waveform control unit 40, which is a base of the ultrasound transmission signal to an ultrasound oscillator array 90. Transmission circuits 10-1 to 10-n output the transmission signal for the required voltage amplitude signal in reference to the transmission reference signal. The transmission signal is applied to ultrasound transducer elements 80-1 to 80-n of the ultrasound oscillator array 90 via transmission lines 100-1 to 100-n. Then the living body as the subject is irradiated with the ultrasound signal via a not shown ultrasound jelly used upon ultrasound irradiation. The reflection ultrasound signal reflecting from the living body is received by the ultrasound transducer element 80-1 to 80-n of the ultrasound oscillator array 90 as well, and further sent to a computation unit 45 via reception lines 110-1 to 110-n, reception circuits 20-1 to 20-n, and analog-digital converters 30-1 to 30-n. The signal is subjected to a predetermined computation in the computation unit 45, and the result is sent to the control circuit 50 so as to display the ultrasound in-vivo image on a display unit 60.

The aforementioned PI method involves the operation of the components from the transmission waveform control unit 40 to the computation unit 45 subsequent to the control circuit 50 as described above. Description in the respective embodiments will be made with respect to the operation carried out by the components from the transmission waveform control unit 40 to the computation unit 45. The transmission waveform control unit 40 and the computation unit 45 are illustrated in simplified manner for explanation purpose, which are not intended to limit the number of function blocks. This applies to the respective embodiments as described below. In the specification, two operation modes including a calibration mode and a diagnostic mode will be described as the operation mode of the ultrasound system. The calibration mode refers to the operation mode for irradiating the predetermined reflection medium with the positive-negative ultrasound based on the PI method prior to the diagnosis so as to acquire correction data for correcting the positive-negative asymmetry. The diagnostic mode refers to the operation mode for irradiating the living body as the subject with the ultrasound so as to acquire the in-vivo ultrasound image. In the description according to the invention, explanation will be made with respect especially to the case for acquiring the ultrasound image (video image) utilizing the PI method. Hereinafter, the modes for carrying out the present invention will be described referring to the drawings. Structures and operations of the respective embodiments will be described hereinafter. The specific explanations of the calibration mode and the diagnostic mode will be made collectively in the latter part of a fourth embodiment.

First Embodiment

A first embodiment relates to an ultrasound system which includes a transmission unit which transmits a first transmission signal and a second transmission signal obtained by polarity inversion of the first transmission signal, an ultrasound probe which transmits an ultrasound based on the first transmission signal and the second transmission signal from the transmission unit, and receives an ultrasound as a reflection ultrasound, a reception unit which receives a first reception signal and a second reception signal corresponding to the first transmission signal and the second transmission signal based on the reflection ultrasound received by the ultrasound probe, and a storage unit which stores correction data for correcting a positive-negative asymmetry based on an addition result of the first reception signal and the second reception signal in a calibration mode. The reception unit executes a correction computation using the addition result of the first reception signal and the second reception signal, and the correction data stored in the storage unit in a diagnostic mode.

A series of structures correct the positive-negative asymmetry including characteristic changes resulting from a transmission signal (electric signal) output from the transmission circuit as the transmission unit, an ultrasound oscillator (electricity-ultrasound interconversion) as the ultrasound probe, and a reception circuit as the reception unit.

Figure 1:
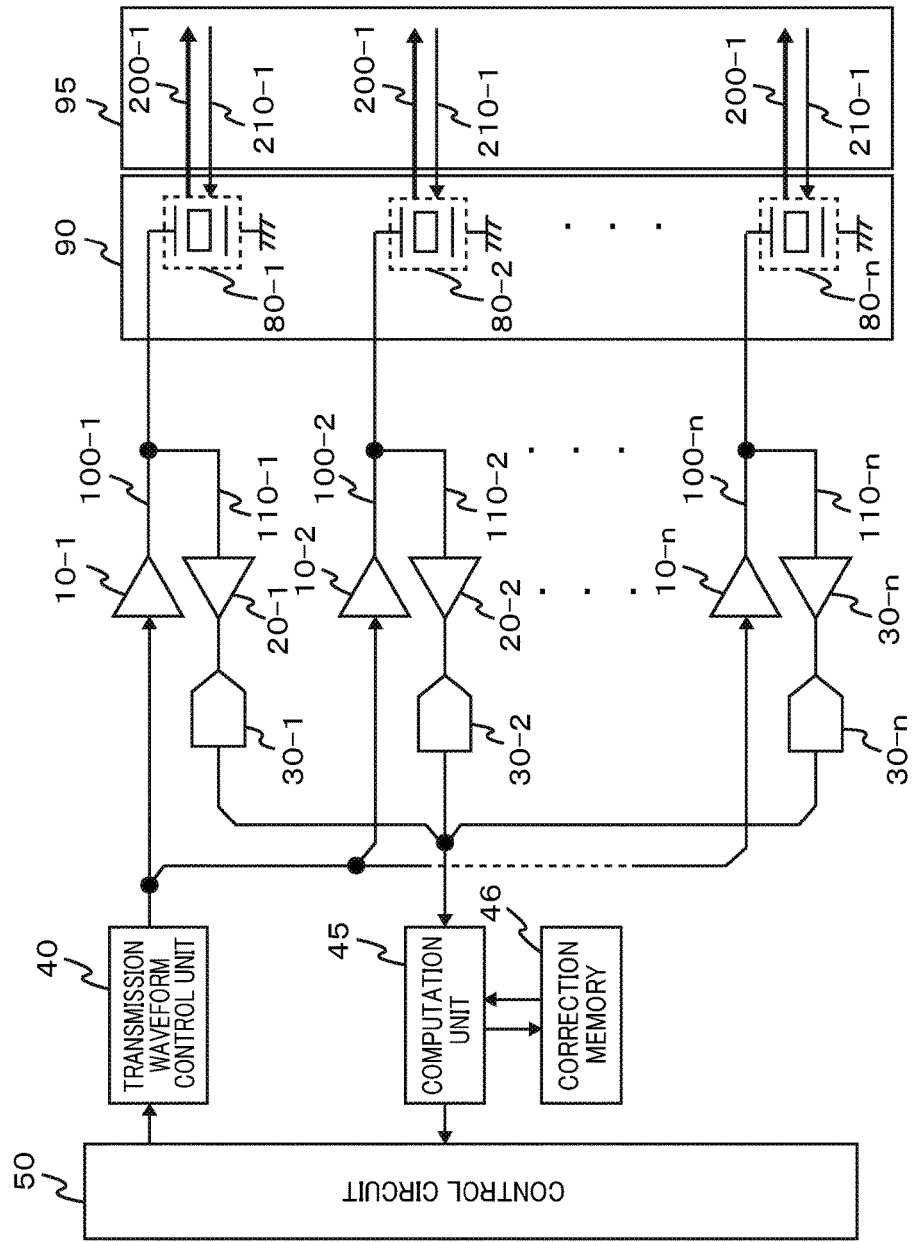
FIG. 1 is a view representing an exemplary structure of an ultrasound transmission-reception circuit according to a first embodiment.

Referring to the structure shown in FIG. 1, the control circuit 50 controls the transmission waveform control unit 40 for applying a transmission signal to the transducer elements 80-1 to 80-$n$ constituting the ultrasound oscillator array 90 via the transmission circuits 10-1 to 10-$n$.

Transmission ultrasounds 200-1 to 200-$n$ generated from the respective transducer elements 80-1 to 80-$n$ of the ultrasound oscillator array 90 are radiated to an irradiation subject via a medium 95 such as the ultrasound jelly used for ultrasound irradiation, which is applied between the ultrasound oscillator array 90 and the body surface in ultrasound inspection. The reflecting ultrasounds 210-1 to 210-$n$ from the irradiation subject are received by the respective transducer elements 80-1 to 80-$n$ of the ultrasound oscillator array 90 via the medium 95 in the similar way. The received reception signal is input to the computation unit 45 via the reception circuits 20-1 to 20-$n$, and analog-digital converters (ADC) 30-1 to 30-$n$. In this case, the medium 95 in the form of ultrasound jelly or gel serves to prevent scattering of air between the ultrasound oscillator array 90 and the body surface.

Figure 2:
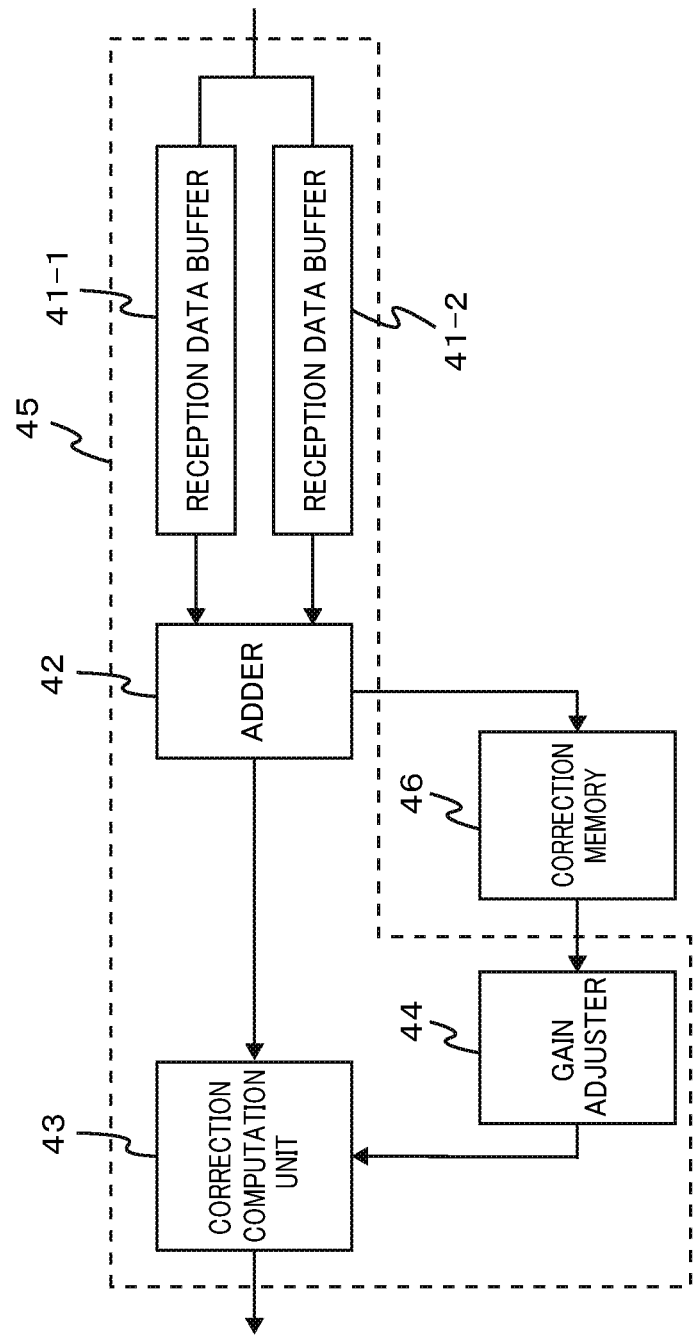
FIG. 2 is a view representing a structure of a computation unit according to the first embodiment.

FIG. 2 is a view representing an example of the inner circuit structure of the computation unit 45 in the reception circuit system according to the embodiment. The first reception data (positive electrode) and the second reception data (negative electrode) are accumulated in reception data buffers 41-1, 41-2, respectively, which are added in an adder 42. In the diagnostic mode, correction is carried out using the correction value preliminarily stored in a correction memory 46 in the calibration mode. The correction value stored in the correction memory 46 is subjected to gain adjustment by a gain adjuster 44 in accordance with depth information of the living body in the diagnostic mode. The embodiment is configured to easily execute the aforementioned process by changing the digital processing unit subsequent to the ADCs 30$a$ to 30$n$ of the main body of the device.

Second Embodiment

Figure 3:
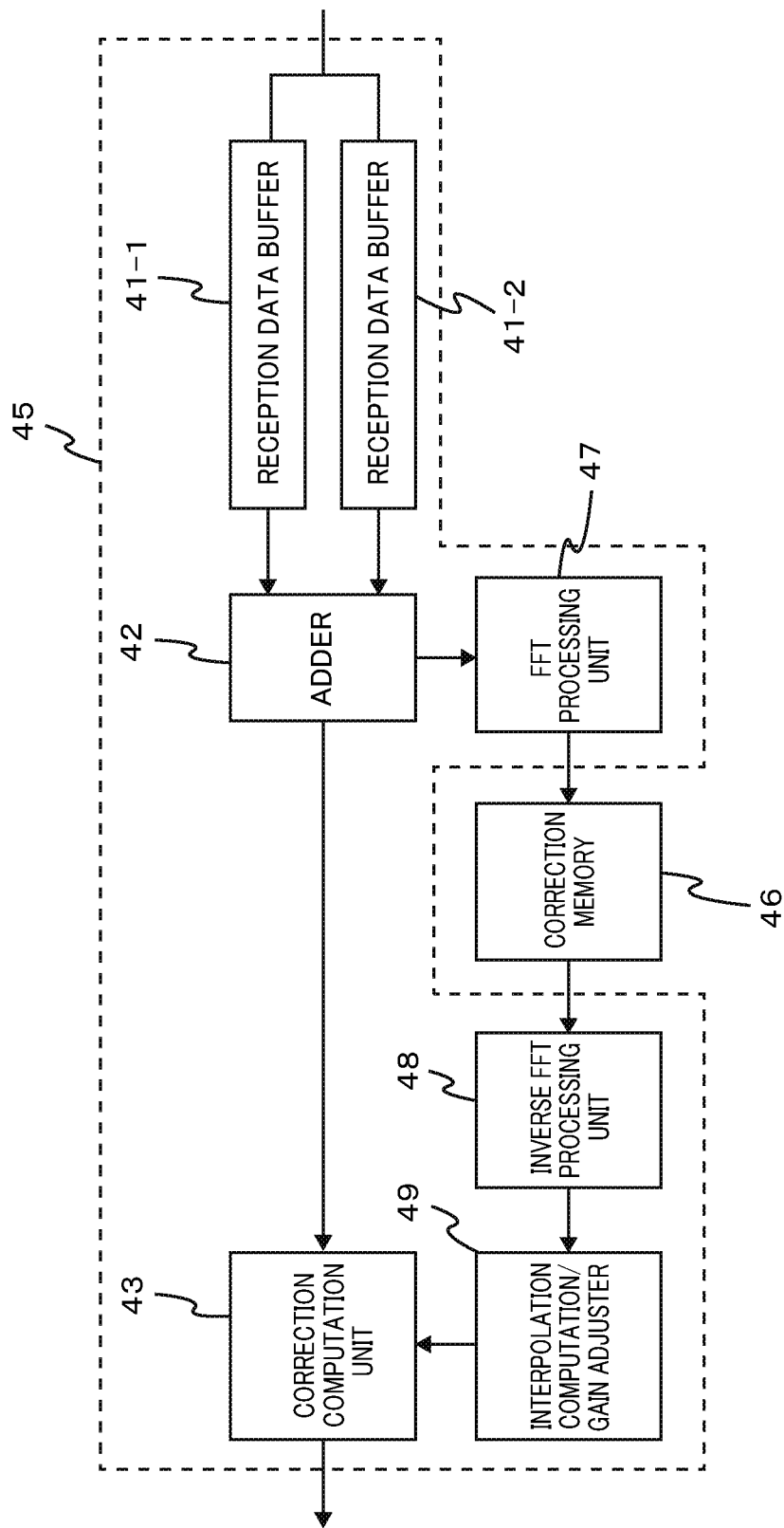
FIG. 3 is a view representing a structure of the computation unit according to a second embodiment.

A computation unit in this embodiment is differently structured from the computation unit 45 of the ultrasound system as described in the first embodiment. FIG. 3 shows a structure of the computation unit 45 as a modified example in the reception circuit system which has been described in the first embodiment. Referring to the drawing, only the structure different from the one shown in FIG. 2 will be described. In the calibration mode, the structure is designed to subject the addition data from the adder 42 to Fourier transformation carried out by an FFT processing unit 47. The resultant data are stored in the correction memory 46. In the diagnostic mode, the correction data in the correction memory 46 are read, and inverse Fourier transformed by an inverse FFT processing unit 48. The resultant data are sent to a correction computation unit 43 via an interpolation computation/gain adjuster 49 for correction.

The embodiment is configured to correct the reception data utilizing fast Fourier transformation (FFT) and inverse fast Fourier transformation (inverse FFT) so that the data with respect only to frequency and magnitude are stored. The embodiment provides the advantage of smaller memory area than that of the first embodiment. In other words, the first embodiment is configured to store data in a time direction, requiring storage of enormous data in accordance with reception time and ADC sampling frequency in the ADC 30, or partially interpolated data. This embodiment is configured to store the data in accordance only with the frequency and magnitude, which makes it possible to reduce the memory area smaller than the first embodiment.

Third Embodiment

An ultrasound system according to this embodiment is configured to have the correction memory for storing the aforementioned correction data disposed at the side of the ultrasound probe.

Figure 4:
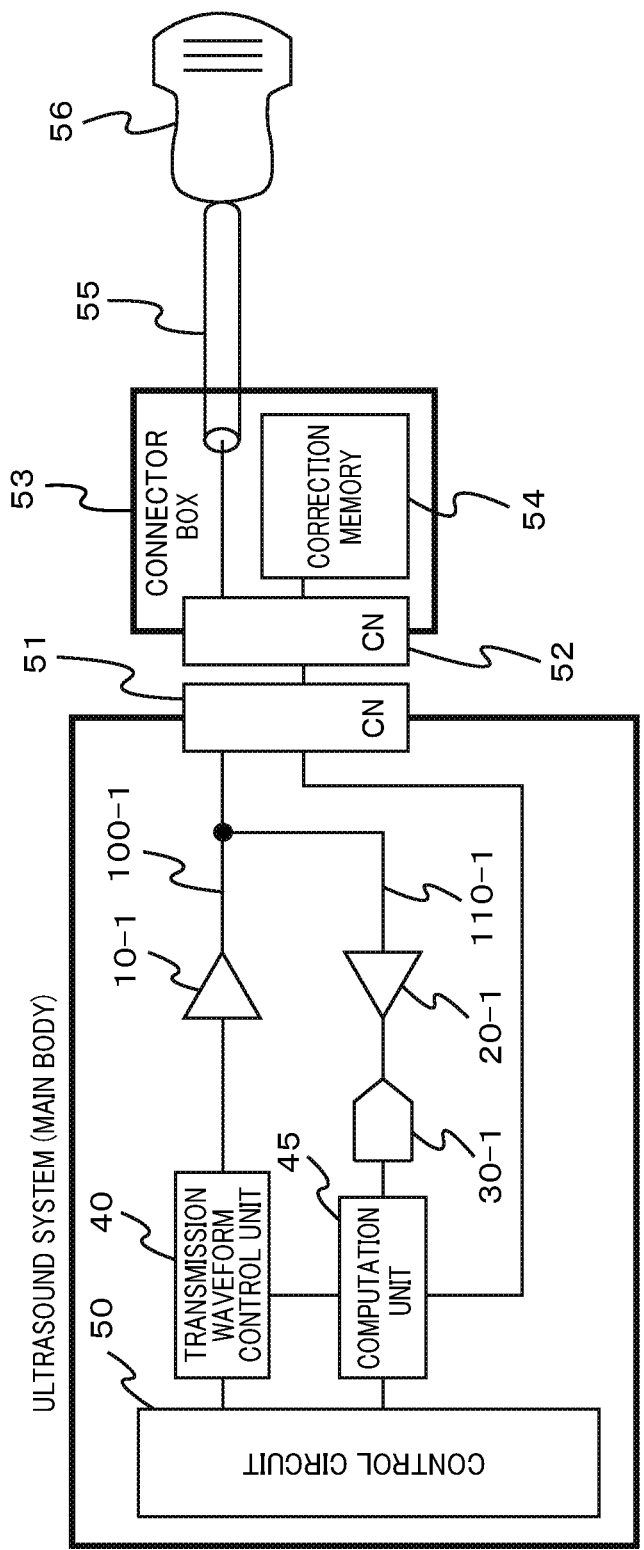
FIG. 4 is a view representing a structure including an ultrasound system and an ultrasound probe according to a third embodiment.

FIG. 4 shows an exemplary structure of the third embodiment. Referring to the drawing, the same components as those described in the first embodiment are designated with the same signs as shown in FIG. 1, and explanations thereof, thus will be omitted. An ultrasound system 300 (main body) and a connector box (BOX) 53 are connected with connectors 51, 52. The ultrasound oscillator array 90 in the overall structure shown in FIG. 1 is disposed at the side of an ultrasound probe 56 in the drawing.

The correction memory 54 for storing the correction data as described above is disposed in the connector BOX 53. The ultrasound reception signal and the correction data are sent to the computation unit 45 of the ultrasound system (main body) via the connectors 51 and 52 so that the correction computation is executed. As the aforementioned process is similar to the one described in the former embodiments, the explanation will be omitted. The connector BOX 53 and the ultrasound probe 56 are connected via a cable 55, which may be collectively called the ultrasound probe. For the computation unit 45, it is possible to employ the corresponding structure according to either the first or the second embodiment.

The structure according to this embodiment necessitates no addition of the memory at the main body side of the ultrasound system to be adapted to the newly developed ultrasound probe. As a result, it is possible to allow the previously purchased ultrasound system to easily realize the high quality image. The device of the aforementioned type includes components for identifying the type of the ultrasound probe such as the microcomputer (MCU) and FPGA (field-programmable gate array) in the connector BOX. Those components may be commonly used with the correction memory 54. It is therefore possible to provide the ultrasound probe with correction memory at lower costs.

Fourth Embodiment

Figure 7:
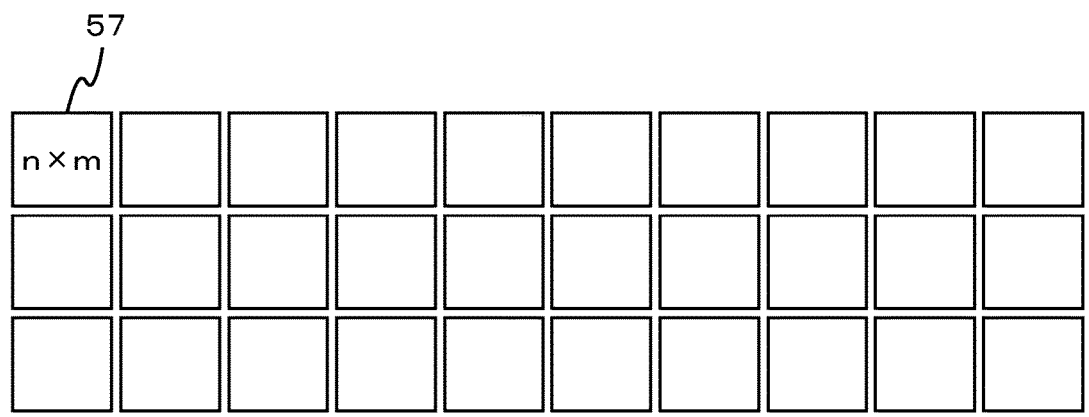
FIG. 7 is a view representing an exemplary structure of an oscillator of a two dimensional (2D) array probe according to a fourth embodiment.

This embodiment describes a 2D array probe of the ultrasound system. FIG. 7 is a schematic front view of the 2D array probe of the embodiment. Referring to FIG. 7, the probe according to the embodiment is constituted by a group of sub-arrays each formed of a plurality of (nxm) oscillators. In the case where the (nxm) oscillators are arranged in 2D array to form the probe, the integrated circuit is connected adjacently to the 2D array. Such structure makes it possible to compensate for the symmetry using the correction data with smaller number than that of the oscillators. The 2D array requires the integrated circuits by the number corresponding to that of oscillators. The integrated circuits allow dispersion between adjacent circuits to be lessened, which allows execution of the calibration mode through restriction of the number of circuits to those at the respective corners and at the center, or thinning out of every other sub-arrays among plural (nxm) sub-arrays. Those thinned-out sub-arrays are subjected to the process to share the correction data acquired by the adjacent oscillator. This makes it possible to execute the correction process equivalently to all the oscillators.

The method of correcting the positive-negative asymmetry, which is carried out in the above-described ultrasound system according to the embodiments will be explained. The ultrasound system according to the respective embodiments includes two operation modes, that is, the calibration mode and the diagnostic mode. The operation flow of the calibration mode executed by the manufacturer or the user of the ultrasound system will be explained referring to FIG. 5. The manufacturer of the device acquires the correction data by following the operation flow executed in the calibration mode upon shipment inspection of the ultrasound system. Meanwhile, the user is allowed to follow the operation flow to acquire the correction data.

Figure 5:
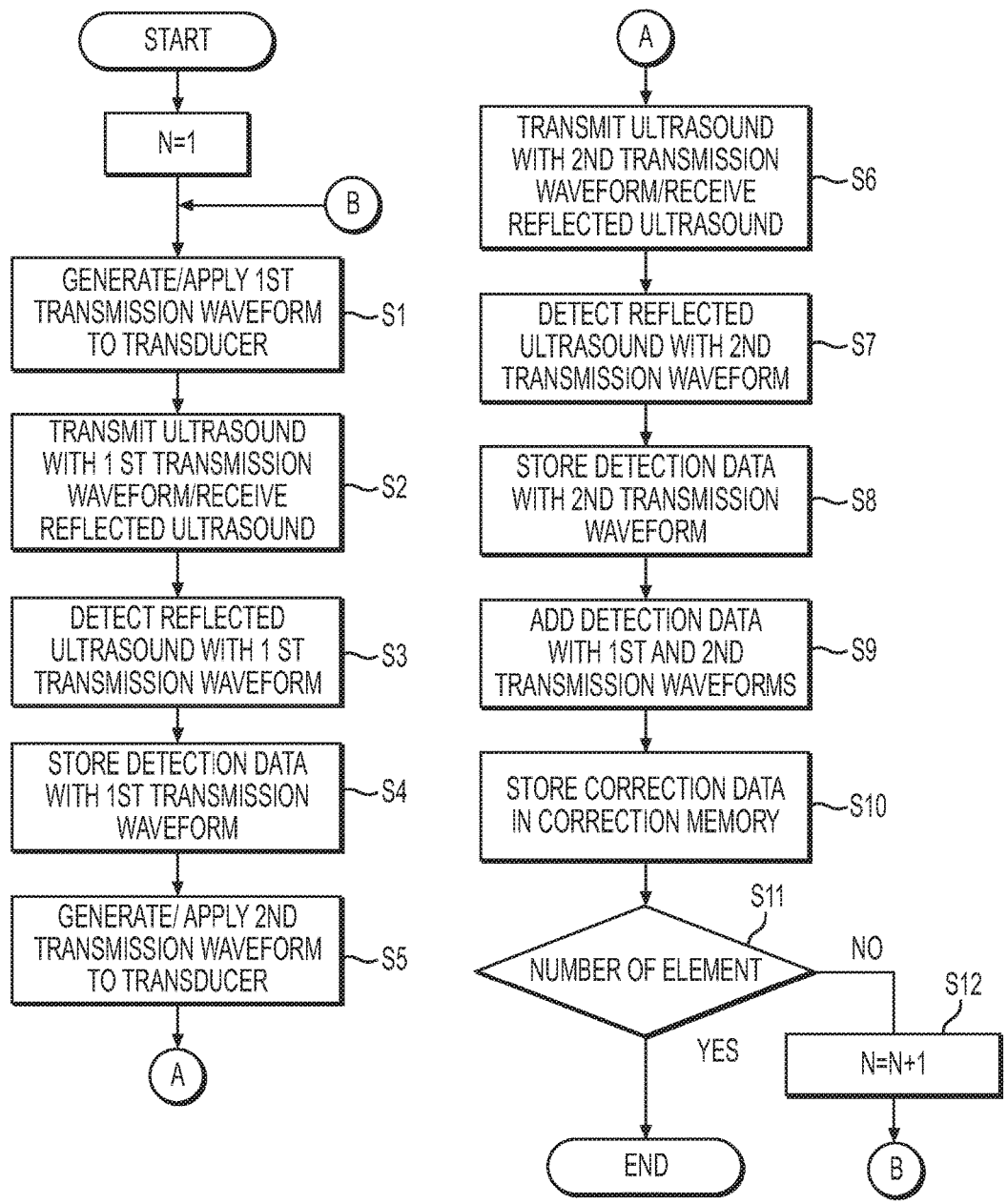
FIG. 5 is a flowchart representing an example of an operation of the ultrasound system according to the respective embodiments.

FIG. 5 represents an example of the operation flow for acquisition of the correction data stored in the correction memory according to the respective embodiments as described above. Signs in the parenthesis may be referred to FIG. 5, and other signs may be typically referred to FIGS. 1 and 3. Referring to FIG. 5, upon start (START) of the acquisition flow under control of the control circuit 50, N=1 is set in a not shown counter so as to output a transmission reference signal to the transmission waveform control unit 40 shown in FIG. 1, which is a base of a first ultrasound transmission signal to the first transducer element 80-1. Then the first transmission waveform is applied to the first transducer elements 80-1 via a first transmission circuit 10-1 (S1). At this timing, the transmission waveform control unit 40 is controlled not to output the transmission reference signal to the second to the nth transmission circuits 10b to 10n, or the second to the nth transmission circuits 10b to 10n are controlled not to output the signal.

Referring to FIG. 5, in the calibration mode, the living body is not irradiated with ultrasound. The transmitted ultrasound is reflected and attenuated by the medium 95 applied onto the surface of the ultrasound oscillator array 90 as shown in FIG. 1 so as to allow the reception circuit systems to detect the received ultrasound. In other words, a first reflection ultrasound (ultrasound echo) 210-1 from the medium 95 is received by the first ultrasound transducer element 80-1 (S2), and input to the computation unit 45 via a first reception circuit system line 110-1, the first reception circuit 20-1, and the first ADC 30-1 so that the reflected ultrasound is detected (S3). The first reflection ultrasound signal is stored in the reception data buffer 41-1 in the computation unit 45 (S4).

Likewise the above-described case, the transmission waveform control unit 40 outputs the transmission reference signal as a base of a second ultrasound transmission signal to the first transducer element 80-1 for generating a second transmission waveform via the first transmission circuit 10-1. It is applied to the first ultrasound transducer elements 80-1 of the ultrasound oscillator array 90 so that the detection data are stored in the data buffer 41-2 (S5 to S8). The stored detection data are added by the adder 42 (S9), and a first addition result with respect to N=1 is stored in the correction memory 46 (S10). In the case where N oscillators, for example, 64 oscillators in a single array constitute the 1D array, the same process steps are repeatedly executed until N reaches 64 (S1 to S10). Then the calibration mode ends (S11, S12). The second transmission waveform is the one derived from polarity inversion of the first transmission waveform, or the phase shift at 180° from the first transmission waveform based on the PI method. The correction data may be acquired by activating the system constituted by a second transmission circuit 10-2, a second transducer element 80-2, and a second reception circuit 20-2 in the case of N=2, or the system constituted by a third transmission circuit 10-3, a third transducer element 80-3, and a third reception circuit 20-3 in the case of N=3. The aforementioned step is intended to eliminate the influence of the adjacent oscillator, resulting from operation of a plurality of oscillators. The aforementioned correction data flow in the calibration mode is a mere example. In the case of the 1D array constituted by the single array of 64 oscillators, it is possible to execute 2-system operation. For example, the system (N=1) including the first transmission circuit 10-1, the first transducer element 80-1, and the first reception circuit 20-1 may be operated simultaneously with the system including the 33rd transmission circuit 10-33, the 33rd transducer element 80-33, and the 33rd reception circuit 20-33. Similarly, the system (N=2) including the second transmission circuit 10-2, the second transducer element 80-2, and the second reception circuit 20-2 may be operated simultaneously with the system including the 34th transmission circuit 10-34, the 33rd transducer element 80-33, and the 33rd reception circuit 20-33. If the oscillators are not arranged adjacently, they are less influenced by the other oscillator. Therefore, simultaneous operation of a plurality of discrete systems ensures reduction in the time for the correction data acquisition in the calibration mode.

Execution of the operation flow in the calibration mode as described above allows acquisition of the correction data for correcting the positive-negative asymmetry including characteristic changes resulting from a transmission signal waveform (electric signal) of the transmission circuit output, the oscillator (electricity-ultrasound interconversion), and the reception circuit in a series of transmission-reception circuit systems. Upon acquisition of the correction data by the user through execution of the operation flow shown in FIG. 5, it is possible to acquire the correction data with high accuracy adapted for change in user's setting of the transmission ultrasound power and frequency. As the user performs the correction in using the device, the highly accurate correction data may be acquired corresponding to the characteristic change owing to environmental fluctuation such as temperature. The ultrasound jelly generally used for inspection of the ultrasound system may be employed as the medium 95, which allows the user to easily acquire the correction data. Furthermore, as the same jelly used for ultrasound irradiation as the one used in the diagnostic mode is employed for correction, the correction error may be reduced.

Figure 6:
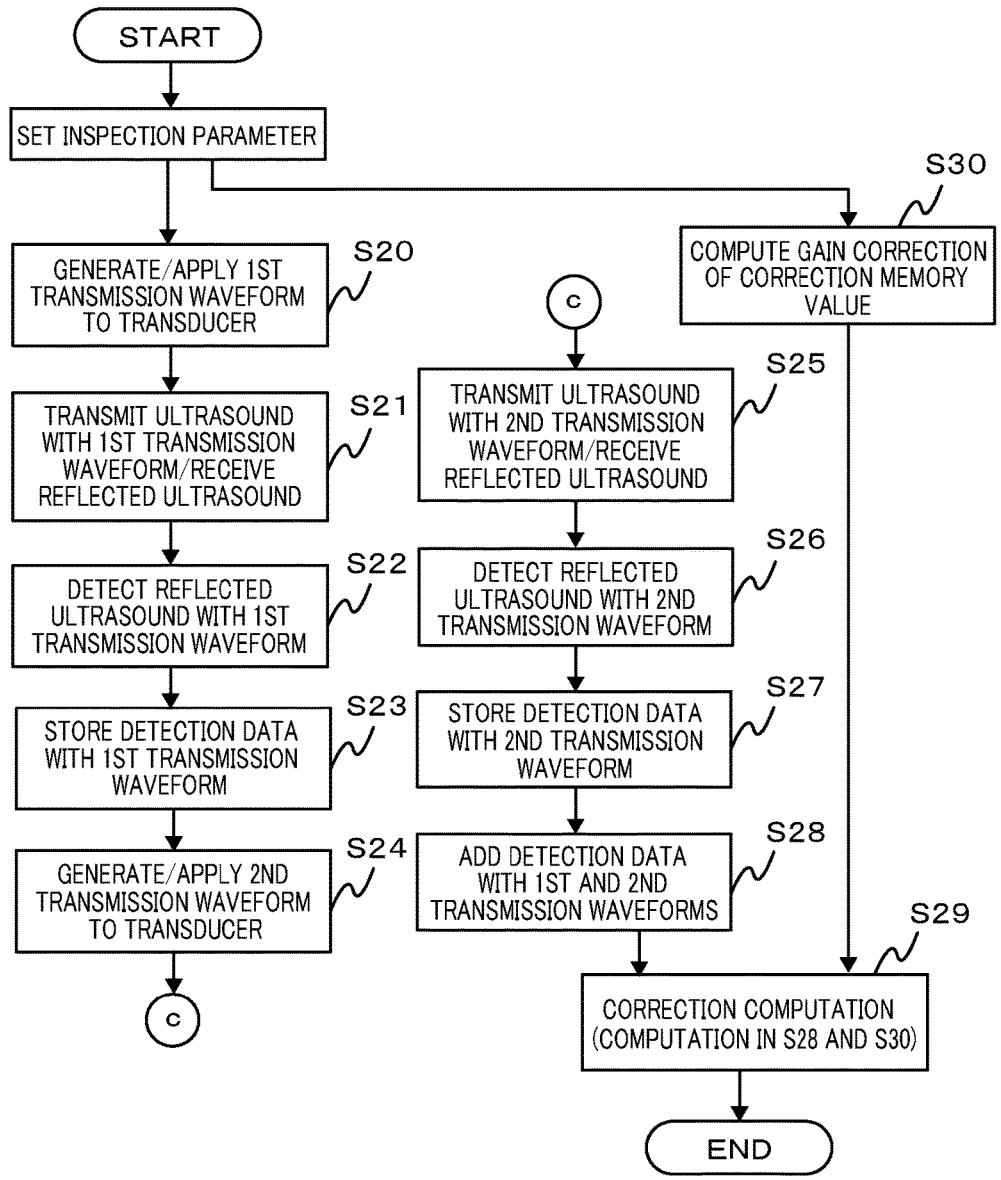
FIG. 6 is a flowchart representing another example of the operation of the ultrasound system according to the respective embodiments.

FIG. 6 represents an example of a diagnostic flow for executing the ultrasound diagnosis to the living body in the ultrasound system according to the embodiment using the correction data stored in the calibration mode. The signs in parenthesis may be referred to FIG. 6, and other signs may be typically referred to FIGS. 1 and 2. Upon start (START) of diagnosis by the ultrasound system, the control circuit 50 sets various inspection parameters. The thus set parameters are used for gain correction carried out by the gain adjuster 44 with respect to the correction data acquired from the correction memory 46 of the above-described computation unit 45 in the calibration mode (S30).

The transmission waveform control unit 40 generates the first transmission reference signal waveform, based on which the first transmission signal is applied to the transducer elements 80-1 to 80-n via the transmission circuits 10-1 to 10-n, respectively (S20). The not shown living body is irradiated with transmission ultrasounds 200-1 to 200-n in accordance with the first transmission waveform via the medium 95. Then reflection ultrasounds 210-1 to 210-n from the living body will be received (S21). The transducer elements 80-1 to 80-$n$ of the ultrasound oscillator array 90 detect (receive) the reflection ultrasounds 210-1 to 210-$n$ in accordance with the first transmission waveform (S22) so as to store the detection data in the reception data buffer 41-1 via the reception circuits 20-1 to 20-$n$, and the ADCs 30-1 to 30-$n$ (S23). Similarly, the transmission waveform control unit 40 generates the second transmission reference signal waveform so that the second transmission signal is applied to the transducer elements 80-1 to 80-$n$ via the transmission circuits 10-1 to 10-$n$, and the detection data are stored in the data buffer 41-2 (S24 to S27). The first and the second transmission signals are those generated based on the PI method. The stored detection data 41$a$, 41$b$ are added by the adder 42 (S28). The addition result is subjected to the correction computation (S29). The correction computation refers to the arithmetic operation based on the addition result in S28 for subjecting the correction data computed for correction in S30 to addition, subtraction, multiplication or division (S29).

This makes it possible to compensate for the positive-negative asymmetry with high accuracy in the signal transmission-reception system of the ultrasound system (main body) and the ultrasound array probe according to the embodiment.

Figure 8:
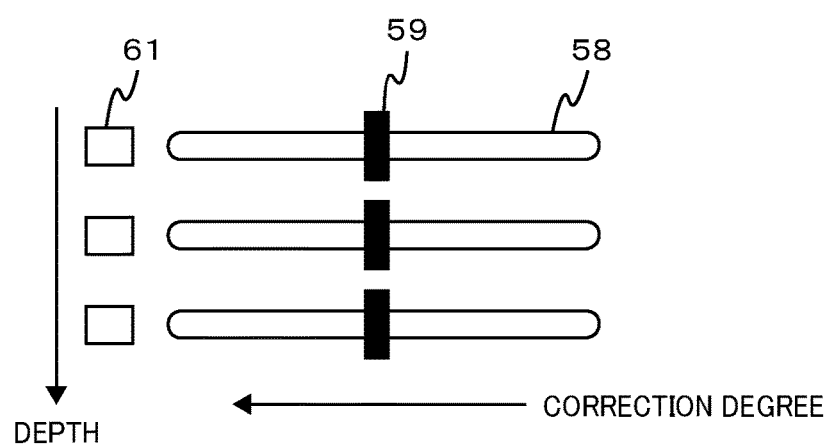
FIG. 8 is a view representing an example of a user adjustment panel according to the respective embodiments.

According to the operation flow shown in FIG. 5, if the correction data are acquired under the representative condition in the product shipment inspection performed by the manufacturer, the gain correction of the correction data by the gain adjuster 44 as shown in FIG. 2 is automatically computed in the ultrasound system in accordance with the inspection parameters set by the user. Provision of a user adjustment panel as shown in FIG. 8 allows the user to check as to application/non-application of the correction data, and perform fine adjustment of the correction value corresponding to the depth in the living body organ. This makes it possible to provide the ultrasound system with further excellent usability.

FIG. 8 shows an exemplary structure of the user adjustment panel for the fine adjustment by the user. As the drawing clearly shows, the adjustment is enabled by checking a check box 61 on the user adjustment panel, which corresponds to the depth of the ultrasound reflection in the subject. Combinations of a scale 58 and a slider 59 are set corresponding to the respective depths, which allow the user to appropriately perform the fine adjustment of the predetermined correction degree in accordance with the depth in the living body. The user adjustment panel may be provided as hardware, or displayed on the display unit 60 as GUI (Graphical User Interface). The user of the ultrasound system is allowed to select the ultrasound image suitable for the diagnosis.

The aforementioned structure allows acquisition of the correction data with high accuracy adapted to the user settings. As the user is allowed to carry out the correction while using the device, the highly accurate correction data may be acquired adapted to the characteristic change resulting from the environmental fluctuation such as temperature. In the case where the user has acquired the correction data, the ultrasound image determined by the user as being suitable for the diagnosis may be acquired by providing the measure for determining application/non-application of the correction value and adjustment.

The ultrasound system according to the present invention allows correction of the positive-negative asymmetry in a series of systems employed for the general diagnosis from the transmission-oscillator (ultrasound transmission) to the oscillator-reception (reflected ultrasound detection). Therefore, the present invention provides the ultrasound system, and the ultrasound probe for realizing the high quality ultrasound image.

The invention is not limited to the embodiments as described above, and may include various modifications. The embodiments have been described in detail for better understanding of the present invention, and are not necessarily restricted to the one provided with all the structures of the description. The structure of any one of the embodiments may be partially replaced with that of the other embodiment. Alternatively, it is possible to add the structure of any one of the embodiments to that of the other embodiment. It is also possible to have the part of the structure of the respective embodiments added to, removed from and replaced with the other structure.

The aforementioned structures, functions and processing units have been explained by means of the operation flow as an example for producing the program which partially or entirely realizes them. It is also clear that they may be partially or entirely realized by hardware designed into the integrated circuit, for example.

REFERENCE SIGNS LIST

10, 10$a$-10$n$ transmission circuit
20-20$n$ reception circuit
30$a$-30$n$ analog to digital converter (ADC)
40 transmission waveform control unit
42 adder
43 correction computation unit
44 gain adjuster
45 computation unit
46,54 correction memory
47 fast Fourier transformer (FFT)
48 inverse FFT
49 interpolation computation/gain adjuster
50 control circuit
51,52 connector (CN)
53 connector box (BOX)
55 cable
56 ultrasound probe
57 sub-array
58 scale
59 slider
60 display unit
61 check box
70 user control unit
80 ultrasound transducer element
90 ultrasound transducer array elements
100,100$a$-100$n$ transmission line
110,110$a$-110$n$ reception line

The invention claimed is:

1. An ultrasound system comprising:
a transmission circuit which transmits a first transmission signal and a second transmission signal obtained by polarity inversion of the first transmission signal;
an ultrasound probe which transmits a first ultrasound signal to an irradiation subject based on the first transmission signal from the transmission circuit, receives a first reflection ultrasound signal from the irradiation subject, transmits a second ultrasound signal to the irradiation subject based on the second transmission signal from the transmission circuit and receives a second reflection ultrasound signal from the irradiation subject;

a reception circuit which receives a first reception signal corresponding to the first reflection ultrasound signal received by the ultrasound probe and a second reception signal corresponding to the second reflection ultrasound signal received by the ultrasound probe;

a memory which stores correction data for correcting a positive-negative asymmetry between the first and second transmission signals based on an addition result of adding the first reception signal and the second reception signal in a calibration mode; and a processor configured to execute a correction computation in which an addition, a subtraction, a multiplication, or a division between the addition result and the correction data stored in the memory is performed in a diagnostic mode to compensate for the positive-negative asymmetry between the first and second transmission signals, wherein the processor performs a Fourier transform on the addition result and an inverse Fourier transform on the correction data.

2. The ultrasound system according to claim 1, wherein: the memory stores data obtained by Fourier transforming the addition result.

3. The ultrasound system according to claim 1, wherein the memory is disposed at a side of the ultrasound probe.

4. The ultrasound system according to claim 1, wherein the ultrasound probe comprises a 2D array of transducer elements.

5. The ultrasound system according to claim 1, further comprising a user adjustment panel which allows adjustment of a correction degree corresponding to the correction data in accordance with a depth of the reflection ultrasound.

6. The ultrasound system according to claim 1, further comprising a display unit configured to display a graphical user interface (GUI) for adjusting a correction degree corresponding to the correction data in accordance with a depth of the reflection ultrasound.

7. The ultrasound system according to claim 1, wherein in the calibration mode, the first and second reflection ultrasound signals received by the ultrasound probe are reflected by a transmission medium applied to the ultrasound probe.

8. An ultrasound diagnostic method comprising the steps of:

receiving, by an ultrasound probe, a first transmission signal and a second transmission signal obtained by polarity inversion of the first transmission signal;

transmitting, by the ultrasound probe, a first ultrasound signal to an irradiation subject based on the first transmission signal and a second ultrasound signal to the irradiation subject based on the second transmission signal;

receiving, by the ultrasound probe, a first reflection ultrasound signal from the irradiation subject in response to the first ultrasound signal and a second reflection ultrasound signal from the irradiation subject in response to the second ultrasound signal; and retaining, in a memory, an addition result derived from adding a first reception signal corresponding to the first reflection ultrasound signal and a second reception signal corresponding to the second reflection ultrasound signal in a calibration mode, as correction data for correcting a positive-negative asymmetry between the first and second transmission signals; and carrying out, by a processor, a correction computation in which an addition, a subtraction, a multiplication, or a division between the addition result and the retained correction data is performed in a diagnostic mode to compensate for the positive-negative asymmetry between the first and second transmission signals, wherein the processor performs a Fourier transform on the addition result and an inverse Fourier transform on the correction data.

9. The ultrasound diagnostic method according to claim 8, wherein data obtained by Fourier transforming the addition result are retained in the memory.

10. The ultrasound diagnostic method according to claim 8, wherein a correction degree corresponding to the correction data is adjusted in accordance with a depth of the first and second reflection ultrasound signals.

11. The ultrasound diagnostic method according to claim 8, wherein the first and second reflection ultrasound signals received by the ultrasound probe in the calibration mode are reflected by a transmission medium applied to the ultrasound probe.

* * * * *